(12) United States Patent
Ueyama et al.

(10) Patent No.: US 8,618,171 B2
(45) Date of Patent: Dec. 31, 2013

(54) ENCAPSULATED OIL-IN-WATER TYPE EMULSION COMPOSITION

(75) Inventors: Tatsuki Ueyama, Kawasaki (JP); Tatsuya Hattori, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 888 days.

(21) Appl. No.: 11/623,978

(22) Filed: Jan. 17, 2007

(65) Prior Publication Data

US 2007/0265347 A1    Nov. 15, 2007

(30) Foreign Application Priority Data

Jan. 18, 2006 (JP) ................................ 2006-010313

(51) Int. Cl.
  *A61K 31/16* (2006.01)
  *A61Q 19/00* (2006.01)
  *B01F 3/08* (2006.01)

(52) U.S. Cl.
  USPC .......................................... 514/616; 516/70

(58) Field of Classification Search
  None
  See application file for complete search history.

(56) References Cited

U.S. PATENT DOCUMENTS

| | | | |
|---|---|---|---|
| 4,818,521 A * | 4/1989 | Tamabuchi | 424/62 |
| 2004/0223996 A1 | 11/2004 | Franklin et al. | |
| 2004/0248812 A1 * | 12/2004 | Hanabusa et al. | 514/18 |
| 2005/0208085 A1 | 9/2005 | Yamato et al. | |
| 2006/0057170 A1 * | 3/2006 | Guiramand | 424/401 |
| 2006/0078581 A1 * | 4/2006 | Yamato | 424/401 |

FOREIGN PATENT DOCUMENTS

| | | | | |
|---|---|---|---|---|
| EP | 0 389 700 A1 | 10/1990 | | |
| EP | 0 992 488 A2 | 4/2000 | | |
| JP | 61-229812 | 10/1986 | | |
| JP | 01172312 | * 1/1989 | | |
| JP | 01-172312 | 7/1989 | | |
| JP | 01-193216 | 8/1989 | | |
| JP | 02-117610 | 5/1990 | | |
| JP | 2-277542 | 11/1990 | | |
| JP | 06-157240 | 6/1994 | | |
| JP | 07-149621 | 6/1995 | | |
| JP | 10-259114 | 9/1998 | | |
| JP | 2005-298388 | * 10/2005 | ............... | A61K 7/00 |
| WO | WO 03/102104 A1 | 12/2003 | | |
| WO | WO 2004105707 | * 12/2004 | ............... | A61K 7/00 |

OTHER PUBLICATIONS

Michalun et al., Skin Care and Cosmetic Ingredients Dictionary, Milady Publishing, Albany, NY, 1994.*
O' Lenick in "Emulsion Using Silicone Emulsifiers" in SiliconeSpectator.com (http://www.siliconespectator.com/articles/Silicone_Spectator_Supplemental_Nov_15_2008.pdf).*
'wax definition' (www.The freedictionary.com/wax).*
'Me p-hydroxybenzoate definition' (medical-dictionary.thefreedictionary.com/methyl+p-hydroxybenzoate).*
Isaak Effendy et al, "Surfactants and experimental irritant contact dermatitis", *Contact Dermatitis*, vol. 33, No. 4, pp. 217-225.
U.S. Appl. No. 12/167,556, filed Jul. 3, 2008, Saito, et al.
U.S. Appl. No. 12/045,260, filed Mar. 10, 2008, Saito, et al.
Searh Report issued Dec. 7, 2010, in French Patent Application No. 0752741 (with English translation of category of cited documents).
Japanese Office Action issued Apr. 5, 2011, in Patent Application No. 2006/010313 (English-language translation only).

* cited by examiner

*Primary Examiner* — Dennis Heyer
(74) *Attorney, Agent, or Firm* — Oblon, Spivak, McClelland, Maier & Neustadt, L.L.P.

(57) ABSTRACT

Encapsulated oil-in-water type emulsion compositions, which comprise an acylamino acid alkylamide or an acyl-glutamine alkyl ester, an oily base, a polar solvent and water, do no exhibit coalescence of the dispersed phase, and can be produced by a simple method without resort to a special apparatus, are excellent in stability with time, do not impart an uncomfortable feeling during application, are excellent in a sensory feeling that satisfies both a moisturizing feeling and an emollient feeling, and are excellent in appearance.

17 Claims, No Drawings

ENCAPSULATED OIL-IN-WATER TYPE EMULSION COMPOSITION

CROSS REFERENCES TO RELATED APPLICATIONS

This application claims priority to Japanese Patent Application No. 010313/2006, filed on Jan. 18, 2006, which is incorporated herein by reference in its entirety.

BACKGROUND OF THE INVENTION

1. Field of the Invention

The present invention relates to encapsulated oil-in-water type emulsion compositions.

2. Discussion of the Background

In the cosmetic field, oil-in-water type emulsions that provide a moisturizing feeling to the skin during use and impart a non-oily feeling have been widely used. However, such emulsions are generally thermodynamically unstable, and have a characteristic that they result in creaming due to a difference in the specific gravity between an oil and water, aggregation caused by collision between particles, and separation into two phases in the end caused by coalescence of the dispersed phase. Accordingly, various trials have been made so far in order to prevent such coalescence of the dispersed phase.

Several attempts to stabilize such emulsions were made by adding a third component. By increasing the amount of an emulsifying agent, an attempt to stabilize such an emulsion was made (see, *Contact Dermatitis*, vol. 33, 4, p. 217 (1955)), however, not only was the prevention of coalescence incomplete, but also a problem arose that a sticky feeling unique to an emulsion was conspicuous.

Further, an attempt to obtain a stabilized emulsion was also made by using a water-soluble thickening agent such as an alkyl-modified carboxyvinyl polymer (see, JP-A-7-149621). However, it did not achieve the prevention of coalescence.

Further, an approach in which a solid or semi-solid oil, a water-soluble thickening agent, an oil-soluble thickening agent are combined was also made (see, JP-A-6-157240). However, a problem in stability arose; a sticky feeling derived from the solid or semi-solid oil component or a slimy feeling derived from the water-soluble thickening agent was caused; it was not a widely-used technique, because an extremely special equipment was required for the production, and so on, and any of the oil-in-water type emulsion compositions were not satisfactory.

On the other hand, an attempt to improve a technique of emulsification was also made. An attempt to form an emulsion particle into a fine particle with a size of 0.3 micrometer or less by carrying out an emulsification treatment under a high pressure of 1000 psi or more was made (see, JP-A-10-259114). However, the softening temperature of the entire oil phase was 50° C. or below, and therefore, the stability thereof at a high temperature was low, and it was not always satisfactory.

Further, several attempts to achieve encapsulation thereof were made actively. Thus, an attempt to utilize the characteristic of an aqueous cosmetic, while preventing the coalescence of the oil phase by a capsule film composed of calcium alginate, was made (see, JP-A-2-117610). However, in such an alginate capsule, the raw material to be blended was limited, it could only be used in a specific pH range, the viscosity was decreased by a polyvalent metal ion used in a curing reaction in the case where an outer phase with low salt resistance was used, and so on, and it was not always satisfactory.

An attempt to achieve stabilization by a soft capsule containing an agar as a base was made (see, JP-A-1-193216). However, when it was applied to the skin as a cosmetic, there was an undeniable sense of a foreign matter that agar debris remained on the skin.

Thus, there remains a need for an encapsulated oil-in-water type emulsion composition in which coalescence of the dispersed phase does not occur, and which can be produced by a simple method without resort to a special apparatus, is excellent in stability with time, does not impart an uncomfortable feeling during application, is excellent in a sensory feeling that satisfies both of a moisturizing feel and an emollient feel and is excellent in appearance.

SUMMARY OF THE INVENTION

Accordingly, it is one object of the present invention to provide novel encapsulated oil-in-water type emulsion compositions.

It is another object of the present invention to provide novel encapsulated oil-in-water type emulsion compositions in which coalescence of the dispersed phase does not occur.

It is another object of the present invention to provide novel encapsulated oil-in-water type emulsion compositions which can be produced by a simple method without resort to a special apparatus.

It is another object of the present invention to provide novel encapsulated oil-in-water type emulsion compositions which are excellent in stability over time.

It is another object of the present invention to provide novel encapsulated oil-in-water type emulsion compositions which do not impart an uncomfortable feeling during application.

It is another object of the present invention to provide novel encapsulated oil-in-water type emulsion compositions which are excellent in a sensory feeling that satisfies both of a moisturizing feeling and an emollient feeling.

It is another object of the present invention to provide novel encapsulated oil-in-water type emulsion compositions which are excellent in appearance.

It is another object of the present invention to provide novel methods for making such an encapsulated oil-in-water type emulsion composition.

These and other objects, which will become apparent during the following detailed description, have been achieved by the inventors' discovery that the above objects can be achieved by preparing an encapsulated oil-in-water type emulsion composition which comprises an acylamino acid alkylamide or an acylglutamine alkyl ester, an oily base, a polar solvent and water.

That is, the present invention includes the following embodiments.

(1) An encapsulated oil-in-water type emulsion composition, which comprises the following components (A), (B), (C), and (D):

(A) one or two or more ingredients selected from the group consisting of an acylamino acid alkylamide and an acylglutamine alkyl ester;

(B) at least one oily base;

(C) at least one polar solvent; and (D) water.

(2) The encapsulated oil-in-water type emulsion composition according to (1), which comprises an acylamino acid alkylamide represented by formula (1):

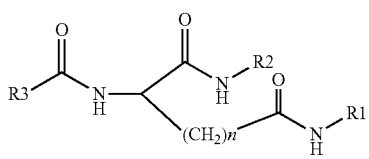

wherein R1 and R2 each independently represent a hydrocarbon group having 1 to 26 carbon atoms, R3 represents a hydrocarbon group having 7 to 11 carbon atoms, and n represents 1 or 2.

(3) The encapsulated oil-in-water type emulsion composition according to (1) or (2), which comprises an ingredient selected from the group consisting of N-2-ethylhexanoyl-L-glutamic acid dibutylamide, N-lauroyl-L-glutamic acid dibutylamide, and N-lauroylglutamine isopropyl ester.

(4) The encapsulated oil-in-water type emulsion composition according to any one of (1) to (3), wherein:
  the weight ratio of the weight of said component (A) to the total weight of said component (B) and said component (C) is in the range of from 0.01:99.99 to 20:80;
  the weight ratio of the weight of said component (B) to the total weight of said component (A) and said component (C) is in the range of from 99:1 to 24:76;
  the weight ratio of the weight of said component (C) to the total weight of said component (A) and said component (B) is in the range of from 70:30 to 0.8:99.2;
  the weight ratio of the weight of said component (D) to the total weight of said component (A), said component (B), and said component (C) is in the range of from 1:99 to 50:50; and
  the gelation (solidification) temperature of the entire oil phase including said component (A), said component (B), and said component (C) is 100° C. or lower.

(5) The encapsulated oil-in-water type emulsion composition according to any one of (1) to (4), further comprising component (E):
  (E) at least one nonionic surfactant.

(6) The encapsulated oil-in-water type emulsion composition according to any one of (1) to (5), further comprising component (F):
  (F) at least one oil-soluble medicinal component.

(7) The encapsulated oil-in-water type emulsion composition according to any one of (1) to (6), further comprising component (G):
  (G) at least one oil dispersible powder.

It has become possible to provide a novel encapsulated oil-in-water type emulsion compositions which are excellent in stability with time, do not impart an uncomfortable feeling during application, are excellent in a sensory feeling that satisfies both a moisturizing feeling and an emollient feeling, and are excellent in appearance, while preventing the coalescence of the dispersed phase, which could not be achieved in an oil-in-water type emulsion composition, and which can be produced by a simple method without resort to a special apparatus. In particular, a silicone oil with which it had been difficult to obtain a stable emulsion composition so far could be stably emulsified, and further, it became possible to stably blend an oil-soluble material therein.

DETAILED DESCRIPTION OF THE PREFERRED EMBODIMENTS

Hereinafter, the constituent elements of the present invention will be described sequentially.

An encapsulated oil-in-water type emulsion composition in the present invention means an emulsion composition comprising water as an outer phase and an oil as an inner phase, and a system in which coalescence of the oil phase does not occur by centrifugation. This is attributed to the oil phase showing an encapsulated structure. Depending on the rate of centrifugation, the stability of coalescence resistance of the encapsulated oil phase is exhibited. Further, the stability against the coalescence of the oil phase also depends on the factors of time, temperature, and force. For example, it refers to those in which coalescence does not occur even if the lower limit of a centrifugal force is 10 G in a centrifugal operation for 1 minute generally at room temperature, preferably at 25° C. From the viewpoint that the stability against coalescence of capsules is high, the lower limit of the centrifugal force is preferably 50 G, more preferably 100 G, further more preferably 200 G, still further more preferably 300 G, especially preferably 500 G, and particularly preferably 1000 G. The upper limit of the centrifugal force is not particularly limited as long as it allows the contents to come out of the capsule in the use thereof as a general cosmetic. However, from the viewpoint that a sense of remaining foreign matter of the capsule components is reduced, the upper limit of the centrifugal force is preferably 1,000,000 G, more preferably 100,000 G, and further more preferably 10,000 G. In a narrow sense, the evaluation criteria of this stability against coalescence is a method of distinguishing that an emulsion composition is an encapsulated oil-in-water type, and in a broad sense, it is a method of distinguishing that an encapsulated oil-in-water is present in a product such as a cosmetic.

As the component A in the invention, one or two or more of an acylamino acid alkylamide and an acylglutamine alkyl ester can be used.

The acylamino acid alkylamide as the component (A) to be used in the present invention can be produced by, for example, producing N-acylated glutamic acid or N-acylated asparatic acid by reacting a long-chain fatty acid halide with L-glutamic acid or L-asparatic acid by the Schotten-Baumann reaction in the presence of a basic catalyst, and then reacting by heating an amine derivative such as an alkyl amine with it in the presence of an acidic catalyst or in the absence of a catalyst. Alternatively, it can be produced by reacting glutamic acid or asparatic acid with an amine derivative such as an alkyl amine in the presence of an acidic catalyst or in the absence of a catalyst, and then N-acylating the resulting glutamic acid amide or asparatic acid amide with an acylating agent such as a fatty acid halide. From the viewpoint that the performance of the composition is most excellent, among acylamino acid alkylamides, an acylamino acid alkylamide represented by the following general formula (1) is preferred.

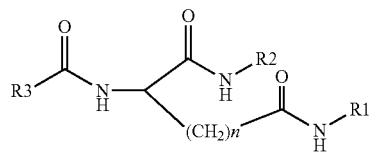

In the formula, R1 and R2 each independently represent a hydrocarbon group having 1 to 26 carbon atoms, R3 represents a hydrocarbon group having 7 to 11 carbon atoms, and n represents 1 or 2.

In the acylamino acid alkylamide (A) represented by the general formula (1) to be used in the present invention, R1 and R2 each independently represent an alkyl group having 1 to 26 carbon atoms. The alkyl groups represented by R1 and R2 may be any of linear, branched, and cyclic alkyl groups, and a combination thereof. Preferably, a linear or branched alkyl group having 1 to 12 carbon atoms, more preferably, a linear or branched alkyl group having 2 to 6 carbon atoms can be used. Further more preferred is a linear or branched alkyl group having 3 to 5 carbon atoms. Most preferably, an n-butyl group can be used.

In the acylamino acid alkylamide represented by the general formula (1) to be used in the present invention, R3 represents a hydrocarbon group having 7 to 11 carbon atoms. The hydrocarbon group represented by R3 may be any of linear, branched, and cyclic alkyl groups. Among them, one type may be used, or two or more types selected from the above-mentioned group may be used in combination. As the hydrocarbon group, a hydrocarbon group containing an unsaturated bond can be used, however, it is more preferred to use an alkyl group. As the alkyl group, a linear or branched alkyl group is preferred. Examples of a group represented by R3—CO— include an n-octanoyl group, an n-nonanoyl group, an n-decanoyl group, an n-undecanoyl group, an n-dodecanoyl group, a 2-ethylhexanoyl group, and the like. Among them, from the viewpoint of exhibiting a high gelation ability for various oily bases, an octanoyl group, a decanoyl group, an n-dodecanoyl group, and a 2-ethylhexanoyl group are preferred, and an n-dodecanoyl group and a 2-ethylhexanoyl group are particularly preferred.

In the acylamino acid alkylamide represented by the general formula (1) to be used in the present invention, when n is 1, an acidic amino acid residue in the molecule represents an L-asparatic acid residue, and when n is 2, it represents an L-glutamic acid residue. From the viewpoint of exhibiting a high gelation ability for an oily base, n is preferably 2. There is a case where the compound represented by the general formula (1) has one or more asymmetric carbons according to the type of R1, R2 and/or R3, however, it may be any of an optical isomer based on such an asymmetric carbon, a steroisomer such as diastereomer, a mixture of arbitrary steroisomers, and a racemic compound. Further, in the case where R1, R2 and/or R3 has an olefinic double bond, its configuration may be either Z and E, and it may be a geometric isomer or a mixture of arbitrary geometric isomers. Further, it may be an arbitrary hydrate of an amino acid derivative represented by the above general formula (1) and a crystal in an arbitrary form. As the amino acid derivative of the present invention, an arbitrary substance such as an isomer or a mixture thereof, or a hydrate thereof described above can be used.

Specific examples of the acylamino acid alkylamide represented by the general formula (1) to be used in the present invention include N-octanoylglutamic acid dibutylamide, N-decanoylglutamic acid dibutylamide, N-lauroylglutamic acid dibutylamide, and N-2-ethylhexanoylglutamic acid dibutylamide. Among them, one type may be used, or two or more types selected from the above-mentioned group may be used in combination. Among them, from the viewpoint of having strength and a good sensory feeling, N-2-ethylhexanoylglutamic acid dibutylamide and N-lauroylglutamic acid dibutylamide are particularly preferred.

The N-acylaminoglutamine alkyl ester as the component A in the invention is a compound represented by the following general formula (2).

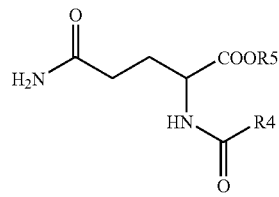

(2)

In the formula, R4 represents a linear or branched hydrocarbon group having 7 to 17 carbon atoms, and R5 represents a linear or branched hydrocarbon group having 2 to 18 carbon atoms.

The hydrocarbon group represented by R4 may be either linear or branched. R4 may be derived from a long chain acyl group, which is represented by R4—CO—, derived from a saturated or unsaturated fatty acid and examples thereof include an octanoyl group, a 2-ethylhexanoyl group, a nonanoyl group, a decanoyl group, a lauroyl group, a myristoyl group, a palmitoyl group, a stearoyl group, and an oleoyl group. The acyl group may be derived from a naturally-occurring mixed fatty acid such as coconut oil fatty acid, caster oil fatty acid, olive oil fatty acid, and palm oil fatty acid or a synthetically obtained fatty acid (including branched fatty acid), as well as from a fatty acid with a single component. They may be used singly or two or more selected from them may be used in combination. From the viewpoint of attaining transparency while maintaining gel strength, it is preferred that two or more of them are used in combination, more preferably two or more selected from the group of a lauroyl group, a myristoyl group, a palmitoyl group, and a stearoyl group are used in combination. Furthermore preferably, two or more selected from the group of a lauroyl group, a myristoyl group, and a palmitoyl group are used in combination, and particularly preferably a lauroyl group and a palmitoyl group are used in combination.

R5 is a linear or branched hydrocarbon group having 2 to 18 carbon atoms, and when R5 is a hydrogen atom or a group having more than 18 carbon atoms, a sufficient gelation ability cannot be obtained. They may be used singly or two or more selected from them may be used in combination. From the viewpoint of the gelation ability, R5 is preferably a linear or branched hydrocarbon group having 3 to 12 carbon atoms, more preferably a linear or branched hydrocarbon group having 3 to 8 carbon atoms, furthermore preferably a branched hydrocarbon group having 3 to 8 carbon atoms, particularly preferably a t-butyl group, a sec-butyl group, and an isopropyl group, and especially preferably an isopropyl group.

Glutamine used in the N-acylglutamine alkyl ester as the component A in the invention may be a DL mixture or an optically active substance such as a D-form or an L-form. They may be used singly or two or more selected from them may be used in combination. From the view point of exhibiting a stable gelation ability, L-glutamine is particularly preferred.

Examples of the N-acylglutamine alkyl ester as the component A in the invention include N-lauroylglutamine isopropyl ester, N-lauroylglutamine sec-butyl ester, N-lauroylglutamine ethyl ester, N-lauroylglutamine n-octyl ester, N-lauroylglutamine lauryl ester, N-palmitoylglutamine isopropyl ester, N-palmitoylglutamine sec-butyl ester, N-palmitoylglutamine ethyl ester, N-myristoylglutamine sec-butyl ester, N-myristoylglutamine isopropyl ester, N-myristoylglutamine ethyl ester, N-stearoylglutamine sec-butyl ester, and N-stearoylglutamine isopropyl ester. From the stand point of exhibiting a practical gel strength even in a small amount, N-lauroylglutamine isopropyl ester, N-lauroylglutamine sec-butyl ester, and N-lauroylglutamine n-octyl ester are preferred; N-lauroylglutamine isopropyl ester and N-lauroylglutamine sec-butyl ester are more preferred; and N-lauroylglutamine isopropyl ester is particularly preferred.

The N-acylglutamine alkyl ester as the component A in the invention can be prepared by combining known art. For example, it can be obtained by preparing an N-acylglutamine though the Schotten-Baumann reaction in which a long-chain fatty acid halide and glutamine are reacted with each other in the presence of a basic catalyst and reacting the N-acylglutamine with an alcohol under heating in the presence or absence of an acid catalyst.

The content of the component (A) to be used in the encapsulated oil-in-water type emulsion composition according to the present invention is not particularly limited as long as it allows the stabilization of the oil phase. However, the component (A) is used at a weight ratio thereof to the total weight of the component (B) and the component (C) in the range of from 0.01:99.99 to 20:80. Here, when the ratio of the weight of the component (A) to the total weight of the component (B) and the component (C) is less than 0.01% by weight, the oil phase cannot be sufficiently stabilized, and when it exceeds 20% by weight, an encapsulated oil-in-water type emulsion cannot be formed in some cases because the component (A) does not completely dissolve in the oil phase. Further, from the viewpoint of the ease of preparation of an encapsulated oil, the weight ratio of the weight of the component (A) to the total weight of the component (B) and the component (C) is in the range of preferably from 0.1:99.9 to 10:90, more preferably from 0.5:99.5 to 7:93.

The oily base (B) to be used in the present invention is not particularly limited as long as it can uniformly disperse the above-mentioned component (A), and a known component to be blended in a cosmetic is generally used. Specific examples thereof include esters such as myristyl myristate, hexyl laurate, decyl oleate, isopropyl myristate, hexyldecyl dimethyloctanoate, glyceryl monostearate, diethyl phthalate, ethylene glycol monostearate, octyl oxystearate, and neopentylene glycol dioctanoate; hydrocarbons such as liquid paraffin and squalane; triglycerides such as glyceryl tricapryl-caprate; fats and oils such as mink oil, cacao oil, palm oil, palm kernel oil, camellia oil, sesame oil, castor oil, and olive oil; silicone oils such as ether-modified silicones including methylpolysiloxane, highly polymerized methylpolysiloxanes, polyoxyethylene-methylpolysiloxane copolymers, polyoxypropylene methylpolysiloxane copolymers, poly(oxyethylene oxypropylene) methylpolysiloxan copolymers and the like, cyclic silicones including stearoxymethylpolysiloxane, stearoxytrimethylsilane, methylhydrogenpolysiloxane, octamethylpolysiloxane, decamethylpolysiloxane, decamethylcyclopentasiloxane, octamethylcyclotetrasiloxane, tetrahydrotetramethylcyclotetrasiloxane, methylcyclopolysiloxane, cyclopentasiloxane, dodecamethylcyclohexasiloxane and the like, amino-modified silicones including 1,1,5,5-tetraphenyltrisiloxane, methylphenylpolysiloxane, trimethylsiloxysilicate, aminoethylaminopropylsiloxane-dimethylsiloxane copolymers and the like, silanol-modified polysiloxanes, alkoxy-modified polysiloxanes, fatty acid-modified polysiloxanes, fluorine-modified polysiloxanes, epoxy-modified polysiloxanes, alkoxy-modified polysiloxane perfluoropolyethers, and polyvinyl acetate dimethylpolysiloxane, and the like. Among these, one type may be used, or two or more types selected from the above group may be used in combination. Here, from the viewpoint that if the component (A) cannot be uniformly dispersed, an encapsulated oil-in-water type emulsion cannot be sufficiently formed, the melting point of the oily base is preferably 60° C. or lower. From the viewpoint of a sticky feeling when it is applied to the skin, an oily base which maintains a liquid state at normal temperature is more preferred.

From the viewpoint of the ease of dissolution of the component (A), the weight ratio of the weight of the component (B) to be used in the encapsulated oil-in-water type emulsion composition of the present invention to the total weight of the component (A) and the component (C) is preferably in the range of from 99:1 to 24:76, and from the viewpoint of the gelation temperature of the oil phase, it is more preferably in the range of from 85:15 to 48:52, and from the viewpoint of the stability of the encapsulated oil-in-water type emulsion at a high temperature, it is further more preferably in the range of from 85:15 to 56:44.

The polar solvent (C) to be used in the present invention is not particularly limited as long as it can sufficiently dissolve the above-mentioned component (A) by heating with the use of the above-mentioned oily base (B) in combination, and a known component to be blended in a cosmetic is generally used. Specific examples thereof include lower alcohols such as ethanol and 2-propanol; higher alcohols such as isostearyl alcohol, lauryl alcohol, myristyl alcohol, cetyl alcohol, stearyl alcohol, hexadecyl alcohol, and octyldodecanol; polyhydric alcohols such as 1,3-butylene glycol, dipropylene glycol, and propylene glycol, and the like. Among these, one type may be used, or two or more types selected from the above group may be used in combination. From the viewpoint that a stable capsule can be provided, a lower alcohol and a higher alcohol are preferred, and a higher alcohol is more preferred, and isostearyl alcohol, lauryl alcohol, myristyl alcohol, cetyl alcohol, stearyl alcohol, hexadecyl alcohol, and octyldodecanol are further more preferred, and isostearyl alcohol and octyldodecanol are particularly preferred.

Here, if the component (A) cannot be dissolved by heating in a mixture of the oily base (B) and the polar solvent (C), an encapsulated oil-in-water type emulsion composition cannot be formed in some cases, which is not preferred. From this viewpoint, the weight ratio of the weight of the component (C) to the total weight of the component (A) and the component (B) is preferably in the range of from 70:30 to 0.8:99.2, and from the viewpoint of the gelation temperature of oily phase, it is more preferably in the range of from 40:60 to 12:88, and from the viewpoint of the stability of the encapsulated oil-in-water type emulsion at a high temperature, it is further more preferably in the range of from 30:70 to 12:88.

The water (D) to be used in the present invention is not particularly limited as long as it has a purity comparable to that of those to be generally used in a washing agent or a cosmetic. Specifically, ion-exchanged water, well water, natural water, groundwater, municipal water, hard water, soft water, or the like can be used. Among these, one type may be used, or two or more types selected from the above group may be used in combination. From the viewpoint of the storage stability of the product of the present invention or the aspect of hygiene, ion-exchanged water is preferred. The weight ratio of the weight of the component (D) to the total weight of the component (A), the component (B) and the component (C) is in the range of from 99:1 to 50:50, and from the viewpoint of the appearance, performance, a refreshing feel after application, it is more preferably in the range of from 99:1 to 70:30, and from the viewpoint of a moisturizing feeling during application, it is further more preferably in the range of from 99:1 to 80:20.

Further, in the present invention, by adding a nonionic surfactant (E), the dispersed state of the encapsulated oil-inwater type emulsion composition can be made stable, and creaming can be prevented from occurring. As the nonionic surfactant (E) to be used in the present invention, any surfactant can be used without being particularly limited as long as it is a nonionic surfactant to be commonly used in the production of a general cosmetic. Specific examples thereof include polyoxyethylene (hereinafter also referred to as POE) (5 to 10 mol) hexadecyl ethers, POE (6 to 9 mol) oleyl ethers, POE (5 to 7 mol) lauryl ethers, POE (5 to 10 mol) isostearyl ethers, POE (8 to 12 mol) dilaurate, POE (6 to 12 mol) monoisostearate, POE (8 to 20 mol) diisostearate, POE (5 to 12 mol) monooleate, POE (3 to 60 mol) glyceryl monostearate, POE (3 to 20 mol) glyceryl tristearate, POE (3 to 60 mol) glyceryl monoisostearate, POE (10 to 60 mol) glyceryl diisostearate, POE (3 to 60 mol) glyceryl triisostearate, POE (20 to 50 mol) glyceryl trioleate, POE (4 to 25 mol) sorbitan monolaurate, POE (5 to 25 mol) sorbitan monococoate, POE (5 to 25 mol) sorbitan monopalmitate, POE (5 to 25 mol) sorbitan monostearate, POE (5 to 25 mol) sorbitan monooleate, POE (5 to 25 mol) sorbitan tristearate, POE (5 to 25 mol) sorbitan trioleate, POE (20 to 40 mol) trimethylolpropane trimyristate, POE (20 to 50 mol) trimethylolpropane triisostearate, POE (5 to 100 mol) hydrogenated castor oil, POE (15 to 50 mol) castor oil, POE (10 to 60 mol) hydrogenated castor oil monolaurate, POE (5 to 60 mol) hydrogenated castor oil monoisostearate, POE (3 to 60 mol) hydrogenated castor oil triisostearate, glyceryl monoisostearate, glyceryl diisostearate, diglyceryl monoisostearate, diglyceryl monooleate, sorbitan monoisostearate, sorbitan sesquiisostearate, sorbitan monooleate, tetraglyceryl monoisostearate, hexaglyceryl monoisostearate, decaglyceryl monoisostearate, hexaglyceryl diisostearate, decaglyceryl diisostearate, decaglyceryl pentaisostearate, and the like. In the present invention, one type or two or more types of these nonionic surfactants (E) can be used.

Further, in the encapsulated oil-in-water type emulsion composition according to the present invention, the HLB value of the nonionic surfactant (E) is not particularly limited, however, it is preferably in the range of from 3.5 to 12. When the HLB value thereof is less than 3.5, an effect on improving the dispersibility of the encapsulated oil in the water phase may become poor, and when it exceeds 12, the solubility of the nonionic surfactant (E) in the oil phase may become poor. From the viewpoint of the stability against the silicone oil, the HLB value thereof is more preferably in the range of from 5.5 to 12. Incidentally, as for a method of calculating the HLB value of the nonionic surfactant (E) in the case where two or more types of nonionic surfactants (E) are included, it is calculated as a weighted average value of HLB obtained by calculation from the HLB values of the respective nonionic surfactants (E) and the weight ratio thereof.

As for the blending amount of the nonionic surfactant (E), it is generally used in an amount in the range of from 0.01 to 20% by weight of the total amount of the encapsulated oil-in-water type emulsion composition. When it is less than 0.01% by weight, it cannot contribute to the stabilization of the dispersed state of the encapsulated oil-in-water type emulsion composition, and when it exceeds 20% by weight, a sticky feeling unique to an emulsion becomes pronounced, therefore, it is not preferred. From the viewpoint that there is no irritation to the skin and a sticky feeling during application can be reduced, the blending ratio is in the range of preferably from 0.1 to 15% by weight, more preferably from 0.2 to 10% by weight, further more preferably from 0.3 to 7% by weight and particularly preferably from 0.5 to 5% by weight, based on the total weight of the encapsulated oil-in-water type emulsion composition.

Further, by employing the present invention, an oil-soluble medicinal component (F), which has poor stability against hydrolysis and was difficult to be blended in the formulation of an oil-in-water type emulsion, can be used. It is a matter of course that an oil-soluble medicinal component (F), which has good stability against hydrolysis, can be used. As the oil-soluble medicinal component (F), any component can be used without being particularly limited as long as it is an oil-soluble medicinal component to be commonly used in the production of a general cosmetic. Specific examples thereof include ultraviolet light absorbers such as p-aminobenzoic acid, octyl methoxy cinnamate, 2,4-dihydroxybenzophenone, and t-butoxy dibenzoyl methane; vitamin A and derivatives thereof; vitamin B group including vitamin B6 hydrochloride, vitamin B6 tripalmitate, vitamin B6 dioctanoate, vitamin B2 and derivatives thereof, vitamin B12, vitamin B15 and derivatives thereof, and the like; vitamin C group including ascorbic acid, ascorbyl sulfate (salt), ascorbyl phosphate, ascorbyl dipalmitate, and the like; vitamin E group including α-tocopherol, β-tocopherol, γ-tocopherol, vitamin E acetate, and the like; vitamins including vitamin D group, vitamin H, pantothenic acid, pantethine, biotin, and the like; nicotinamide, benzyl nicotinate, γ-orizanol, allantoin, glycyrrhizinate (salt), glycyrrhezinic acid and derivatives thereof, hinokitiol, bisabolol, eucalyptol, thymol, inositol, saponins such as saikosaponin and carrot saponin, agents and powders of pantothenyl ethyl ethers, ethynyl estradiol, tranexamic acid, arbutin, cepharanthin, placenta extract, and the like. As for the blending amount thereof, it can be used in an amount in the range which allows it to be dissolved in a mixture of the component (A), the component (B), and the component (C). However, from the viewpoint of the solubility in the oil phase, it is preferably in the range of from 0.01 to 10% by weight of the total amount of the encapsulated oil-in-water type emulsion composition, and from the viewpoint of the long-term storage stability, it is more preferably in the range of from 0.01 to 5% by weight based on the total weight of the encapsulated oil-in-water type emulsion composition.

Further, by employing the present invention, an oil dispersible powder (G), which was difficult to be blended in the formulation of an oil-in-water type emulsion, can be used. As the oil dispersible powder, any powder can be used without being particularly limited as long as it is an oil dispersible powder to be commonly used in the production of a general cosmetic. Specific examples thereof include titanium oxide whose surface has been subjected to a hydrophobic treatment, zinc oxide whose surface has been subjected to a hydrophobic treatment, water-insoluble pigments, oil-soluble dyestuffs, oil dispersible ultraviolet light absorbers, and the like. As for the blending amount thereof, it can be used in an amount in the range which allows it to be dispersed in a mixture of the component (A), the component (B), and the component (C). However, from the viewpoint of the ease of dispersion in the oil phase, it is preferably in the range of from 0.01 to 7% by weight of the total amount of the encapsulated oil-in-water type emulsion composition, and from the viewpoint of the long-term storage stability, it is more preferably in the range of from 0.01 to 5% by weight, based on the total weight of the encapsulated oil-in-water type emulsion composition.

The average particle size of the oil phase of the encapsulated oil-in-water type emulsion composition is not particularly limited, and it can be controlled by an addition method and a stirring method during preparation. Further, the shape of the oil phase is not particularly limited, however, from the viewpoint of the good appearance and easiness of the production, it is preferably in a spherical shape.

A production method according to the present invention will be described below.

A first step) A mixture (Z) containing the component (A), the component (B) and the component (C) is dissolved by heating and stirring.

A second step) The mixture (Z) is added to the component (D) under heating while stirring.

A third step) By cooling the mixture while stirring, a desired encapsulated oil-in-water type emulsion composition is obtained.

The order of the addition of the component (A), the component (B), and the component (C) in the first step is not particularly limited. In the case where an oil-soluble substance with poor stability is added, it is preferably added after the mixture (Z) is dissolved, and immediately before the second step. The heating temperature in the first step is not particularly limited as long as the mixture (Z) is dissolved, however, from the viewpoint of the comprehensive evaluation of the resulting composition, it is preferably in the range of from 50 to 180° C., more preferably from 80 to 140° C. The stirring rate in the first step is not particularly limited as long as the mixture (Z) is dissolved.

The heating temperature of the component (D) in the second step is not particularly limited as long as an encapsulated oil in water emulsion is formed, however, from the viewpoint that the shape of the capsule exhibits a spherical shape with relatively uniform size, it is preferably in the range of from 0 to 100° C., more preferably from 50 to 95° C., and particularly preferably from 60 to 90° C. From the viewpoint that a fine encapsulated oil in water emulsion can be obtained, it is preferably not lower than the gellation temperature of the mixture (Z). The heating temperature of the component (D) in the second step relative to the heating temperature of the mixture (Z) is not particularly limited as long as an encapsulated oil in water emulsion can be formed, however, from the viewpoint that a uniform encapsulated oil in water emulsion can be formed, it is preferably in the range of from −30 to 30° C., more preferably from −20 to 20° C., further more preferably from −10 to 10° C., and particularly preferably from −5 to 5° C. The stirring rate in the second step is not particularly limited as long as an encapsulated oil in water emulsion can be formed, however, from the viewpoint that a fine encapsulated oil in water emulsion can be obtained, it is preferably 100 rpm or more. When the stirring rate is too high, capsules collide with one another and the shape of the capsule does not exhibit a spherical shape with a relatively uniform size, therefore, it is preferably 10000 rpm or less. A dropping nozzle in the second step is not particularly limited as long as an encapsulated oil in water emulsion can be formed. In the second step, by controlling the stirring rate or the dropping nozzle, an arbitrary size of encapsulated oil in water emulsion can be selected.

The cooling rate in the third step is not particularly limited as long as an encapsulated oil in water emulsion can be formed. However, in order to form a uniform encapsulated oil in water emulsion, the cooling rate is preferably less than 100° C./min.

In the encapsulated oil-in-water type emulsion composition of the present invention, a variety of components that can be used in a general cosmetic or an external preparation for skin can be appropriately blended to such an extent that the effect of the present invention is not impaired. For example, ionic surfactants, nonionic surfactants, moisturizing agents, powders, pigments, oil agents, antioxidants, thickening agents, membrane back agents, organic solvents, preservatives, chelating agents, fragrances, and the like can be exemplified.

The encapsulated oil-in-water type emulsion composition of the present invention can be used as a cosmetic and a washing agent. For example, basic skin care products such as general creams, emulsions (cleansing creams, cold creams, vanishing creams, hand creams, and the like), skin lotions (hand lotions, general skin lotions, and the like) and facial masks; sunburn/sunscreen skin care products such as sunburn/sunscreen creams and sunburn/sunscreen lotions; hair care products such as hair treatments (hair treatments in the form of a cream, a lotion, a gel, or another form, and including coating preparations for split ends) and hair setting preparations (setting lotions, curler lotions, hair liquids, hair foams, and hair gels); cosmetics for washing such as face washes (in the form of a cream, a paste, a liquid, a gel, or the like) and shampoos, and the like can be exemplified. In particular, from the viewpoint that a clear and stabilized emulsion can be obtained, a clear cosmetic is preferred, and a clear basic skin care product, a clear sunburn/sunscreen skin care product is more preferred.

Other features of the invention will become apparent in the course of the following descriptions of exemplary embodiments which are given for illustration of the invention and are not intended to be limiting thereof.

EXAMPLES

Resulting encapsulated oil-in-water-type emulsion compositions were evaluated in terms of the both stability and sensory aspects by the following evaluation methods and based on the evaluation standards.

Stability Evaluation Method.

1) Appearance

An encapsulated oil-in-water type emulsion composition (Example) and an oil-in-water type emulsion composition (Comparative example) were stored at room temperature (25° C.) for 3 days, and then the appearance thereof was visually observed.

○: The dispersed phase (oil phase) is clear.

Δ: The dispersed phase (oil phase) is not clear.

x: Separation occurs in the dispersed phase (oil phase).

2) Stability Against External Pressure

A 1 ml portion of each of an encapsulated oil-in-water type emulsion composition (Example) and an oil-in-water type emulsion composition (Comparative example) was transferred to a 1.5-mL eppendorf tube, and by using a centrifuge (manufactured by Sigma, Loboratory Centrifuge type 1-13, radius of rotor: 3.5 cm, maximum rotation speed: 13000 rpm), centrifugation was carried out at room temperature for 1 minute while the rotation speed was changed, and then, the separation condition of the oil phase was evaluated based on the following criteria. The gravitational acceleration (RCF) was calculated using the following numerical formula (1).

$$RCF = 1118 \times r \times N^2 \times 10^{-8} (G) \quad (1)$$

r: rotation radius (cm)

N: revolutions per minute (rpm)

⊙: Coalescence of the oil phase occurs at a gravitational acceleration of 1000 G or more and less than 10000 G.

○: Coalescence of the oil phase occurs at a gravitational acceleration of 250 G or more and less than 1000 G.

Δ: Coalescence of the oil phase occurs at a gravitational acceleration of 100 G or more and less than 250 G.

x: Coalescence of the oil phase occurs at a gravitational acceleration of less than 100 G.

3) Stability Against Temperature

An encapsulated oil-in-water type emulsion composition (Example) and an oil-in-water type emulsion composition (Comparative example) were stored at 50° C. for 3 days, and then the emulsion condition thereof was evaluated based on the following criteria.

⊙: Separation does not occur at room temperature and at 50° C., and the composition is stable.

○: The composition is stable at room temperature, and separation occurs at 50° C.

Δ: Slight separation occurs (to an extent that a ring is formed) at room temperature, and separation occurs at 50° C.

x: Separation occurs completely at room temperature and at 50° C.

Sensory Evaluation Method

By 6 special panelists, sensory evaluation was carried out when an encapsulated oil-in-water type emulsion composition (Example) or an oil-in-water type emulsion composition (Comparative example) was applied to the forearm in terms of the respective items of a moisturizing feeling during application, a sense in which there is no sense of a foreign matter (such as a sense of remaining debris) upon application, a natural moist feeling (a sense in which there is no sticky feel) after application.

Evaluation Points

1) A Moisturizing Feeling During Application

| | |
|---|---|
| It gives a very moisturizing feeling as if water were applied. | 4 |
| It gives some oily feeling, however, it gives a moisturizing feeling. | 3 |
| It gives a strong oily feeling. | 2 |
| It gives a very strong oily feeling, but no moisturizing feeling. | 1 |

2) A Sense in which there is No Sense of a Foreign Matter (Such as a Sense of Remaining Debris) Upon Application

| | |
|---|---|
| It gives no sense of a foreign matter. | 4 |
| It gives some sense of a foreign matter, but it does not bother. | 3 |
| It gives a strong sense of a foreign matter. | 2 |
| It gives a very strong sense of a foreign matter and a pain upon application. | 1 |

3) A Natural Moist Feeling after Application

| | |
|---|---|
| It gives a very moist feeling. | 4 |
| It gives a moist feeling to a certain degree. | 3 |
| It gives a sticky feeling. | 2 |
| It gives a very sticky feeling. | 1 |

Evaluation Criteria

⊙: An average evaluation point is 3.5 or more.

○: An average evaluation point is 2.5 or more and less than 3.5.

Δ: An average evaluation point is 1.5 or more and less than 2.5.

x: An average evaluation point is less than 1.5.

Examples 1 to 2 and Comparative Examples 1 to 4

According to the formulation shown in Table 1, an encapsulated oil-in-water type emulsion composition (Example) and an oil-in-water type emulsion composition (Comparative example) were prepared. Then, according to the above-mentioned evaluation methods, evaluation was carried out in terms of the appearance, stability against external pressure, stability against temperature, and sensory feeling. Incidentally, as for the production method, while an aqueous phase portion was heated at 80° C. and stirred at 400 rpm, an oil phase portion which was dissolved by heating at 90° C. was added to the aqueous phase at 2 mL/min, and then, the mixture was let stand to cool at 100° C./h, whereby an emulsion composition was obtained. Incidentally, the preparation was carried out on a 100 g scale. The respective evaluation results are also shown in Table 1.

TABLE 1

(% by weight)

| | | Example | | Comparative Example | | | |
|---|---|---|---|---|---|---|---|
| | | 1 | 2 | 1 | 2 | 3 | 4 |
| Oil Phase | Isopropyl myristate | 5 | — | 5 | — | 5 | — |
| | Cyclomethicone | — | 5 | — | 5 | — | 5 |
| | Octyldodecanol | 1.5 | 1.5 | 1.5 | 1.5 | 1.5 | 1.5 |
| | Ethanol | 0.7 | 0.7 | | | | |
| | N-2-ethylhexanoyl-glutamic acid dibutylamide | 0.15 | 0.15 | | | | |
| | Behenyl alcohol | — | — | — | — | 0.15 | 0.15 |
| Aqueous Phase | Purified water | balance | balance | balance | balance | balance | balance |
| | Total | 100 | 100 | 100 | 100 | 100 | 100 |
| Result | Stability Appearance | ○ | ○ | X | X | Δ | X |
| | Stability against external pressure | ○ | ○ | X | X | Δ | X |
| | Stability against temperature | ⊙ | ⊙ | X | X | ○ | Δ |
| | Sensory feeling Moisturizing feeling during application | ⊙ | ⊙ | X | X | X | X |
| | Sense in which there is no sense of a foreign matter | ⊙ | ⊙ | ⊙ | ⊙ | Δ | Δ |
| | Natural moist feeling after application | ⊙ | ⊙ | Δ | Δ | X | X |

From these results, it was found that the encapsulated oil-in-water type emulsion composition (Example 1) of the present invention can provide a composition which is clear and excellent in stability and a sensory feeling. Further, it was found that it does not give an uncomfortable feeling during application which is observed in a general composition in the form of a capsule.

Example 3 and Comparative Examples 5 to 11

According to the formulation shown in Table 2, an encapsulated oil-in-water type emulsion composition (Example) and an oil-in-water type emulsion composition (Comparative example) were prepared by using liquid paraffin as an oily base and a nonionic surfactant. Then, according to the above-mentioned evaluation methods, evaluation was carried out in terms of the stability against external pressure, stability against temperature, and sensory feeling. Incidentally, as for the production method, while an aqueous phase portion was heated at 80° C. and stirred at 250 rpm, an oil phase portion which was dissolved by heating at 80 to 120° C. was added to the aqueous phase at 2 mL/min, and then, the mixture was let stand to cool at 100° C./h, whereby an emulsion composition was obtained. Incidentally, the preparation was carried out on a 100 g scale. The respective evaluation results are also shown in Table 2 (in the table bak. Means "balance").

TABLE 2

| | | Ex. | Comparative Example | | | | | | (% by weight) |
|---|---|---|---|---|---|---|---|---|---|
| | | 3 | 5 | 6 | 7 | 8 | 9 | 10 | 11 |
| Oil Phase | Liquid paraffin | 5 | 5 | 5 | 5 | 5 | 5 | 2 | 2 |
| | Octyldodecanol | 1.2 | 1.2 | 1.2 | 1.2 | 1.2 | 1.2 | 0.48 | 0.18 |
| | POE (58) hydrogenated castor oil isostearate *1 | 0.75 | 0.75 | 0.75 | 0.75 | 0.75 | 0.75 | 0.3 | 0.3 |
| | N-2-ethylhexanoyl-glutamic acid dibutylamide | 0.06 | — | — | — | — | — | — | — |
| | Behenyl alcohol | — | — | 2 | — | — | — | — | 0.8 |
| | 12-Hydroxystearic acid | — | — | — | 0.3 | — | — | — | — |
| | Dextrin fatty acid ester gelling agent *2 | — | — | — | — | 0.3 | — | — | — |
| | Oligoester gelling agent *3 | — | — | — | — | — | 0.3 | — | — |
| Aqueous Phase | Alkyl acrylate/methacrylate copolymer *4 | — | — | — | — | — | — | 0.1 | 0.1 |
| | Triethanolamine | — | — | — | — | — | — | 0.1 | 0.1 |
| | Purified water | bal. | bal. | bal. | bal. | bal. | bal. | bal. | bal. |
| | Total | 100 | 100 | 100 | 100 | 100 | 100 | 100 | 100 |
| Result | Stability | Stability against external pressure | ◉ | X | X | X | X | Δ | Δ | X |
| | | Stability against temperature | ◉ | X | X | X | X | X | ○ | ○ |
| | Sensory feeling | Moisturizing feeling during application | ◉ | ○ | X | X | Δ | Δ | X | X |
| | | Sense in which there is no sense of a foreign matter | ◉ | ◉ | Δ | ○ | ○ | Δ | Δ | Δ |
| | | Natural moist feeling after application | ◉ | ○ | Δ | X | X | X | Δ | X |

*1: Emalex RWIS-158 (Nihon Emulsion Co., Ltd.)
*2: Rheopearl MKL (Chiba Seifun Co., Ltd.)
*3: Nomcort HK-G (Nisshin Oil Mills Co., Ltd.)
*4: Pemulen TR-1 (Noveon Inc.)

From these results, it was found that the encapsulated oil-in-water type emulsion composition (Example 3) of the present invention is very superior in terms of the emulsion stability and the sensory feeling compared with the conventional oil-in-water type emulsion compositions (Comparative examples 5 to 11). Further, it is a very big advantage that a new application feeling which is different from that of the case of a conventional oil-in-water type emulsion was obtained by altering the oil phase into the encapsulated oil phase thereby delaying the adhesion of the oil components to the skin upon application.

Example 4 and Comparative Examples 12 to 13

According to the formulation shown in Table 3, an encapsulated oil-in-water type emulsion composition (Example) and an oil-in-water type emulsion composition (Comparative example) were prepared by using cyclomethicone as an oily base. Then, according to the above-mentioned evaluation methods, evaluation was carried out in terms of the stability against external pressure, emulsion stability against temperature, and sensory feeling. Incidentally, as for the production method, while an aqueous phase portion was heated at 80° C. and stirred at 250 rpm, an oil phase portion which was dissolved by heating at 80 to 140° C. was added to the aqueous phase at 2 mL/min, and then, the mixture was let stand to cool at 100° C./h, whereby an emulsion composition was obtained. Incidentally, the preparation was carried out on a 100 g scale. The respective evaluation results are also shown in Table 3.

TABLE 3

|  |  |  | (% by weight) | | |
|---|---|---|---|---|---|
|  |  | Example | Comparative Example | | |
|  |  | 4 | 12 | 13 |
| Oil Phase | Cyclomethicone | 3.2 | 3.2 | 3.2 |
|  | Isostearyl alcohol | 1 | 1 | 1 |
|  | PEG-20 glyceryl triisostearate *5 | 0.75 | 0.75 | 0.75 |
|  | N-2-ethylhexanoylglutamic acid dibutylamide | 0.05 | — | — |
|  | Behenyl alcohol | — | — | 1 |
| Aqueous Phase | Purified water | balance | balance | balance |
|  | Total | 100 | 100 | 100 |
| Result | Stability | stability against external pressure | ○ | X | X |
|  |  | stability against temperature | ⊙ | X | X |
|  | Sensory feeling | Moisturizing feeling during application | ⊙ | ○ | X |
|  |  | Natural moist feel after application | ⊙ | ○ | Δ |

*5: Emalex GWIS-320 (Nihon Emulsion Co., Ltd.)

From these results, it was found that even in the case where cyclomethicone with poor emulsion stability was used, the encapsulated oil-in-water type emulsion composition is very superior in terms of the emulsion stability and the sensory feeling compared with the conventional oil-in-water type emulsion compositions. Further, it is a very big advantage that a new application feeling which is different from that of the case of a conventional oil-in-water type emulsion was obtained by altering the oil phase into the encapsulated oil phase thereby delaying the adhesion of the oil components to the skin upon application.

Hereinafter, specific examples of the compositions according to the present invention will be shown.

TABLE 4

Example 5: Whitening cream

| Component | % by weight |
|---|---|
| X Liquid paraffin | 3.2 |
| Isostearyl alcohol | 1.0 |
| Dimethicone copolyol *6 | 0.2 |
| N-2-ethylhexanoylglutamic acid dibutylamide | 0.1 |
| Y Ascorbyl dipalmitate | 0.5 |
| Perfume | appropriate amount |
| Z Glycerine | 3.0 |
| PCA-Na | 0.2 |
| Methylparaben | appropriate amount |
| Purified water | balance |
| Total | 100 |

*6: Emalex SS-5050K (Nihon Emulsion Co., Ltd.)

Production Method

An oil phase portion of X was dissolved by heating and cooled to 80° C. Then, Y was added thereto and dissolved therein. Thereafter, to Z which was heated to 80° C., the mixture of X+Y was added, and the resulting mixture was let stand to cool while stirring, whereby an encapsulated oil-in-water type emulsion composition was obtained. The obtained whitening cream exhibited a good sensory feeling.

TABLE 5

Example 6: Sunscreen milk

| Component | % by weight |
|---|---|
| X Cyclomethicone | 3.0 |
| Isononyl Isononanoate | 1.0 |
| Isostearyl alcohol | 1.5 |
| POE (20) sorbitan trioleate *7 | 0.5 |
| N-2-ethylhexanoylglutamic acid dibutylamide | 0.05 |
| Y Buthyl methoxydibenzoylmethane | 0.5 |
| Titanium oxide | 0.5 |
| Perfume | appropriate amount |
| Z Methylparaben | appropriate amount |
| Purified water | balance |
| Total | 100 |

*7: NIKKOL TO-30 (Nikko Chemicals Co., Ltd.)

Production Method

An oil phase portion of X was dissolved by heating and cooled to 80° C. Then, Y was added thereto and dissolved therein. Thereafter, to Z which was heated to 80° C., the mixture of X+Y was added, and the resulting mixture was let stand to cool while stirring, whereby an encapsulated oil-in-water type emulsion composition was obtained. The obtained sunscreen milk exhibited a good sensory feeling.

TABLE 6

Example 7: Transparent sunscreen lotion

| Component | % by weight |
|---|---|
| X Liquid paraffin | 10.0 |
| Octyldodecanol | 2.0 |
| N-2-ethylhexanoylglutamic acid dibutylamide | 0.2 |
| Y Octyl methoxy cinnamate | 0.5 |
| Perfume | appropriate amount |
| Z Methylparaben | appropriate amount |
| Purified water | balance |
| Total | 100 |

Production Method

An oil phase portion of X was dissolved by heating and cooled to 80° C. Then, Y was added thereto and dissolved therein. Thereafter, to Z which was heated to 80° C., the mixture of X+Y was added, and the resulting mixture was let stand to cool while stirring, whereby an encapsulated oil-in-water type emulsion composition was obtained. The obtained clear sunscreen lotion exhibited a good sensory feeling and a clear sense.

TABLE 7

Example 8: Liquid foundation

| Component | % by weight |
|---|---|
| X Liquid paraffin | 8.0 |
| Hexyldecanol | 8.0 |
| N-lauroylglutamine isopropyl ester | 0.5 |
| Y Talc | 4.0 |
| Titanium dioxide | 5.0 |
| Yellow iron oxide | 0.1 |
| Black iron oxide | 0.5 |

TABLE 7-continued

Example 8: Liquid foundation

| | Component | % by weight |
|---|---|---|
| Z | Propylene glycol | 10.0 |
| | Methylparaben | appropriate amount |
| | Purified water | balance |
| | Total | 100 |

Production Method

An oil phase portion of X was dissolved by heating and cooled to 70° C. Then, thoroughly mixed Y was added to Z which was heated to 70° C. and X was added to Y+Z which were heated to 70° C., and the resulting mixture was let stand to cool while stirring, whereby an encapsulated oil-in-water type emulsion composition was obtained. The obtained liquid foundation exhibited a good sensory feeling.

INDUSTRIAL APPLICABILITY

According to the present invention, it is possible to provide a novel encapsulated oil-in-water type emulsion composition and further a cosmetic which are excellent in stability with time, do not impart an uncomfortable feeling during application, are excellent in a sensory feeling that satisfies both of a moisturizing feeling and an emollient feeling and are excellent in appearance while preventing the coalescence of the dispersed phase, which could not be achieved in a conventional oil-in-water type emulsion composition, and which can be produced by a simple method without resort to a special apparatus. In particular, industrial applicability thereof as a clear cosmetic such as a clear basic skin care product or a clear sunburn/sunscreen skin care product is high.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. An encapsulated oil-in-water type emulsion composition, comprising components (A), (B), (C) and (D):
   (A) an acylamino acid alkylamide represented by formula (1):

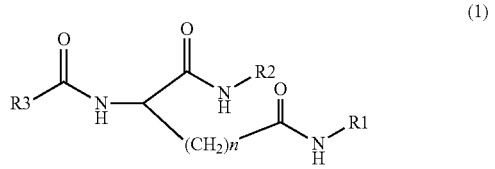

(1)

wherein R1 and R2 each independently represent a hydrocarbon group having 1 to 26 carbon atoms, R3 represents a hydrocarbon group having 7 to 11 carbon atoms, and n represents 1 or 2;
   (B) at least one oily base selected from the group consisting of decyl oleate, isopropyl myristate, hexyldecyl dimethyloctanoate, octyl oxystearate, neopentylene glycol dioctanoate liquid paraffin, squalane, mink oil, cacao oil, camellia oil, sesame oil, olive oil, and silicone oils;
   (C) at least one higher alcohol selected from the group consisting of isostearyl alcohol, lauryl alcohol, myristyl alcohol, cetyl alcohol, stearyl alcohol, hexadecyl alcohol, and octyldodecanol; and
   (D) water;
   wherein:
   components (A), (B), and (C) form an encapsulated oily phase that is dispersed in component (D);
   a weight ratio of a weight of component (A) to a total weight of component (B) and component (C) is in a range of from 0.01:99.99 to 20:80;
   a weight ratio of a weight of component (B) to a total weight of component (A) and component (C) is in a range of from 99:1 to 24:76;
   a weight ratio of a weight of component (C) to a total weight of component (A) and component (B) is in a range of from 70:30 to 0.8:99.2;
   a weight ratio of a weight of component (D) to a total weight of component (A), component (B), and component (C) is in a range of from 99:1 to 50:50;
   a gelation (solidification) temperature of the oil phase is 100° C. or less; and
   an oil phase of the emulsion does not coalesce when a gravitational acceleration of less than 200 G is applied.

2. The encapsulated oil-in-water type emulsion composition according to claim 1, which comprises an ingredient selected from the group consisting of N-2-ethylhexanoyl-L-glutamic acid dibutylamide, N-lauroyl-L-glutamic acid dibutylamide, and N-lauroylglutamine isopropyl ester.

3. The encapsulated oil-in-water type emulsion composition according to claim 1, further comprising component (E):
   (E) at least one nonionic surfactant.

4. The encapsulated oil-in-water type emulsion composition according to claim 2, further comprising component (E):
   (E) at least one nonionic surfactant.

5. The encapsulated oil-in-water type emulsion composition according to claim 1, further comprising component (F):
   (F) at least one oil-soluble medicinal component.

6. The encapsulated oil-in-water type emulsion composition according to claim 2, further comprising component (F):
   (F) at least one oil-soluble medicinal component.

7. The encapsulated oil-in-water type emulsion composition according to claim 3, further comprising component (F):
   (F) at least one oil-soluble medicinal component.

8. The encapsulated oil-in-water type emulsion composition according to claim 1, further comprising component (G):
   (G) at least one oil dispersible powder.

9. The encapsulated oil-in-water type emulsion composition according to claim 2, further comprising component (G):
   (G) at least one oil dispersible powder.

10. The encapsulated oil-in-water type emulsion composition according to claim 3, further comprising component (G):
    (G) at least one oil dispersible powder.

11. The encapsulated oil-in-water type emulsion composition according to claim 5, further comprising component (G):
    (G) at least one oil dispersible powder.

12. The encapsulated oil-in-water type emulsion composition according to claim 1, wherein the component (A) causes an oil phase of the oil-in-water type emulsion composition to be encapsulated.

13. The encapsulated oil-in-water type emulsion composition according to claim 1, wherein the component (A) causes gellation of an oil phase of the oil-in-water emulsion composition.

14. The encapsulated oil-in-water type emulsion composition according to claim 1, wherein the composition is obtained by a method comprising:
   heating and stirring a mixture comprising component (A), component (B), and component (C), to obtain a solution;
   combining the solution and component (D) while stirring under heat, to obtain a mixture; and
   cooling the mixture while stirring, to obtain the encapsulated oil-in-water type emulsion composition.

15. The encapsulated oil-in-water type emulsion composition according to claim 14, wherein combining the solution and component (D) while stirring under heat comprises maintaining the combined solution and component (D) at a temperature of 100° C. or less while stirring.

16. The encapsulated oil-in-water type emulsion composition according to claim 1, wherein component (B) comprises at least one silicone oil selected from the group consisting of methylpolysiloxanes, highly polymerized methylpolysiloxanes, polyoxyethylene-methylpolysiloxane copolymers, polyoxypropylene methylpolysiloxane copolymers, poly(oxyethylene oxypropylene)methylpolysiloxane copolymers, stearoxymethylpolysiloxane, stearoxytrimethylsilane, methylhydrogenpolysiloxane, octamethylpolysiloxane, decamethylpolysiloxane, decamethylcyclopentasiloxane, octamethylcyclotetrasiloxane, tetrahydrotetramethylcyclotetrasiloxane, methylcyclopolysiloxane, cyclopentasiloxane, dodecamethylcyclohexasiloxane, 1,1,5,5-tetraphenyltrisiloxane, methylphenylpolysiloxane, trimethylsiloxysilicate, aminoethylaminopropylsiloxane-dimethylsiloxane copolymers, silanol-modified polysiloxanes, alkoxy-modified polysiloxanes, fatty acid-modified polysiloxanes, fluorine-modified polysiloxanes, epoxy-modified polysiloxanes, alkoxy-modified polysiloxane perfluoropolyethers, and polyvinyl acetate dimethylpolysiloxane.

17. A method of making an encapsulated oil-in-water type emulsion composition according to claim 1,
   said method comprising:
   (1) heating and stirring a mixture of said component (A), said component (B), and said component (C), to obtain a solution;
   (2) combining said solution and component (D) under heating while stirring, to obtain a mixture; and
   (3) cooling said mixture while stirring, to obtain said encapsulated oil-in-water type emulsion composition.

* * * * *